United States Patent [19]

Boon-Falleur et al.

[11] Patent Number: 5,763,165

[45] Date of Patent: Jun. 9, 1998

[54] METHOD FOR DETERMINING LUNG ADENOCARCINOMAS BY ASSAYING FOR ONE OR MORE OF MAGE-1, MAGE-2 AND MAGE-3

[75] Inventors: Thierry Boon-Falleur; Patrick Weynants; Bernard Lethé; Francis Brasseur; Marie Marchand; Charles DeSmet; Christophe Lurquin; Pierre van der Bruggen; Etienne DePlaen, all of Brussels, Belgium

[73] Assignee: Ludwig Institute for Cancer Research, New York, N.Y.

[21] Appl. No.: 209,172

[22] Filed: Mar. 10, 1994

[51] Int. Cl.$^6$ ................................ C12Q 1/68; C12P 19/34
[52] U.S. Cl. ................................ 435/6; 435/91.2
[58] Field of Search .................. 435/6, 91.2; 935/77, 935/78

[56] References Cited

U.S. PATENT DOCUMENTS 5,342,774  8/1994  Boon et al. ..................... 435/240.2

FOREIGN PATENT DOCUMENTS 9220356  11/1992  WIPO.

OTHER PUBLICATIONS

Smet et al. Immunogenetic 39:121–129 (1994).

Van der Bruggen, et al., "A Gene Encoding An Antigen Recognized By Cytolytic T Lymphocytes On A Human Melanoma", Science 254: 1643–1647 (Feb. 13, 1991).

Brasseur, et al., "Human Gene MAGE–1, which codes for a tumor–rejection antigen, is expressed by some tumors", Int. J. Cancer 52: 839–841 (1991).

Primary Examiner—Stephanie W. Zitomer
Assistant Examiner—Eggerton Campbell
Attorney, Agent, or Firm—Felfe & Lynch

[57] ABSTRACT

A method for determining lung adenocarcinomas is described. The method involves assaying for expression of a gene coding for at least one of tumor rejection antigen precursors MAGE-1, 2 and 3, or their expression product.

11 Claims, 2 Drawing Sheets

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

CGGCCGAAGG AACCTGACCC AG        22

( 2 ) INFORMATION FOR SEQ ID NO: 2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 2:

GCTGGAACCC TCACTGGGTT GCC        23

( 2 ) INFORMATION FOR SEQ ID NO: 3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 3:

AAGTAGGACC CGAGGCACTG        20

( 2 ) INFORMATION FOR SEQ ID NO: 4:

( i ) SEQUENCE CHARACTERISTICS:
        ( A ) LENGTH: 20 base pairs
        ( B ) TYPE: nucleic acid
        ( C ) STRANDEDNESS: single -continued ( D ) TOPOLOGY: linear ( x i ) SEQUENCE DESCRIPTION: SEQ ID NO: 4:

GAAGAGGAAG AAGCGGTCTG 20

( 2 ) INFORMATION FOR SEQ ID NO: 5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 5:

TGGAGGACCA GAGGCCCCC 19

( 2 ) INFORMATION FOR SEQ ID NO: 6:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 6:

GGACGATTAT CAGGAGGCCT GC 22

METHOD FOR DETERMINING LUNG ADENOCARCINOMAS BY ASSAYING FOR ONE OR MORE OF MAGE-1, MAGE-2 AND MAGE-3

FIELD OF THE INVENTION

This invention relates to cancer diagnosis. More particularly, it relates to the so-called "tumor rejection antigen precursors" referred to as MAGE-1, 2 and 3, which have been identified as "markers" for certain cancers, lung adenocarcinomas in particular.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum⁻ variants fail to form progressive tumors because they initiate an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl. Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl. Acad. Sci. USA 74: 272–275 (1977); Van Pel et al., supra; Uyttenhove et al., supra).

Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearon et al., Cancer Res. 48: 2975–1980 (1988) in this regard.

A class of antigens has been recognized which are presented on the surface of tumor cells and are recognized by cytolytic T cells, leading to lysis. This class of antigens will be referred to as "tumor rejection antigens" or "TRAS" hereafter. TRAs may or may not elicit antibody responses. The extent to which these antigens have been studied, has been via cytolytic T cell characterization studies in vitro, i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including minor histocompatibility antigens, the male specific H-Y antigens, and the class of antigens referred to as "tum⁻" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of tum⁻ variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $k^d$.

PCT application PCT/US92/04354, filed on May 22, 1992 assigned to the same assignee as the subject application, teaches a family of human tumor rejection antigen precursor coding genes, referred to as the MAGE family, and their expression in various tumor types. Lung adenocarcinoma is not among these. Several of these genes are also discussed in van der Bruggen et al., Science 254: 1643 (1991). It is now clear that the various genes of the MAGE family are expressed in tumor cells, and can serve as markers for the diagnosis of such tumors, as well as for other purposes discussed therein. See also Traversari et al., Immunogenetics 35: 145 (1992); van der Bruggen et al., Science 254: 1643 (1991). The mechanism by which a protein is processed and presented on a cell surface has now been fairly well documented. A cursory review of the development of the field may be found in Baringa, "Getting Some 'Backbone': How MHC Binds Peptides", Science 257: 880 (1992); also, see Fremont et al., Science 257: 919 (1992); Matsumura et al., Science 257: 927 (1992); Latron et al., Science 257: 964 (1992). These papers generally point to a requirement that the peptide which binds to an MHC/HLA molecule be nine amino acids long (a "nonapeptide"), and to the importance of the first and ninth residues of the nonapeptide.

Studies on the MAGE family of genes have now revealed that, in some cases a nonapeptide is presented on the surface of tumor cells, and that the presentation of the nonapeptide requires that the presenting molecule be HLA-A1. Complexes of the MAGE-1 tumor rejection antigen (the "TRA" or nonapeptide") leads to lysis of the cell presenting it by cytolytic T cells ("CTLs"). Additional research has correlated other nonapeptides derived from MAGE and genes to HLA-A1 and other MHC class I molecules.

Research presented in, e.g., U.S. patent application Ser. No. 07/938,334 filed Aug. 31, 1992, showed that, when comparing homologous regions of various MAGE genes to the region of the MAGE-1 gene coding for the relevant nonapeptide, there is a great deal of homology.

The nucleic acid sequences which code for the nonapeptides were also described therein. These nucleic acid sequences were described as also being useful as diagnostic probes for tumor presence.

The application also showed how it had been found that a cellular model could be used, wherein a non-human cell can be transfected with a nucleic acid sequence coding for a human HLA molecule. The resulting transfectant could then be used to test for nonapeptide specificity of the particular HLA molecule, or as the object of a second transfection with a MAGE gene. The co-transfectant could be used to determine whether the particular MAGE based TRA is presented by the particular HLA molecule.

Many of the references referred to supra present data on the expression pattern of various MAGE genes in different types of cell lines and tumor tissues. What is evident from these data is that there is no "unifying principle" which allows one to predict which MAGE gene will be expressed by a particular tumor type. Thus, while on one level one can say that MAGE genes are "markers" for tumors, on the level of specific tumor types, the correlation of marker and tumor type is not predictable, and must be determined empirically.

This invention relates to the identification of expression of MAGE-1, MAGE-2 and MAGE-3 in lung adenocarcinomas. Methods for determining presence of lung adenocarcinoma are the subject matter of the invention.

DETAILED DESCRIPTION OF PREFERRED EMBODIMENTS

EXAMPLE 1

Figure 1:
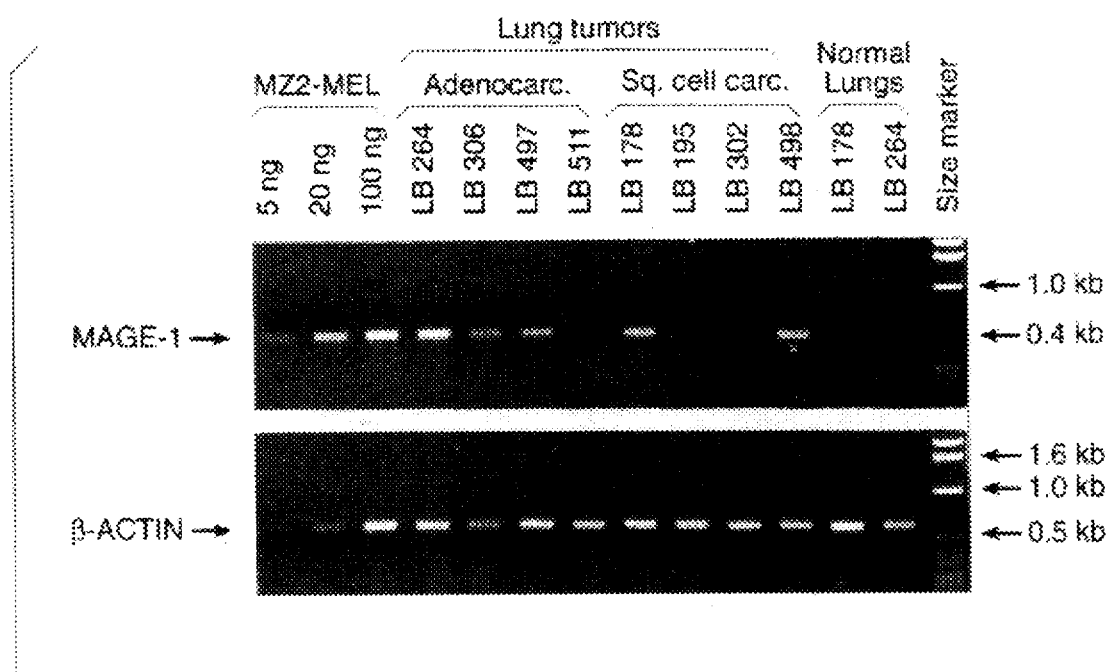
FIG. 1 shows results secured from qualitative PCR assays for MAGE-1.

The expression of the MAGE-1, 2 and 3 genes in various tumors and normal tissues was evaluated, using both reverse transcription and polymerase chain reaction ("PCR") amplification. To perform these assays, the total RNA of the cells of interest was extracted via the well known guanidine-isothiocyanate procedure of Davis et al., Basic Methods in Molecular Biology, 1986 (New York, Elsevier, pp. 130), which is incorporated by reference in its entirety cDNA was then synthesized, by taking 2 ug of the RNA, diluting it with water, and then adding the following materials: 4 ul of 5X reverse transcriptase buffer, 1 ul each of each dNTP (10 mM), 1 ul of a 40 µM solution of oligo dT(15), 20 units of RNAsin, 2 ul of 0.1M dithiothreitol, and 200 units of MoMLV reverse transcriptase. All materials were mixed in a 20 ul reaction volume, and incubated at 42° C. for 60 minutes and diluted to 100 ul with water. Presence or absence of each of MAGE-1, -2, and -3 cDNA was detected via PCR amplification, in separate reactions, using oligonucleotide primers located in different exons of the MAGE gene of interest.

For MAGE-1, the primers were:

| | |
|---|---|
| 5'-CGGCCGAAGGAACCTGACCCAG-3' | (SEQ ID NO: 1) |
| 5'-GCTGGAACCCTCACTGGGTTGCC-3' | (SEQ ID NO: 2) |

These are described by Brasseur et al., Int. J. Cancer 52: 839–841 (1992).

For MAGE-2, the primers were:

| | |
|---|---|
| 5'-AAGTAGGACCCGAGGCACTG-3' | (SEQ ID NO: 3) |
| 5'-GAAGAGGAAGAAGCGGTCTG-3' | (SEQ ID NO: 4) |

(DeSmet et al., Immunogenetics 39: 121–129 (1994)).

For MAGE-3, the primers were:

| | |
|---|---|
| 5'-TGGAGGACCAGAGGCCCCC-3' | (SEQ ID NO: 5) |
| 5'-GGACGATTATCAGGAGGCCTGC-3' | (SEQ ID NO: 6) |

(Ser. No. 08/204,727 filed Mar. 1, 1994 to Gaugler et al.) incorporated by reference.

For each PCR reaction, 5 ul of cDNA were supplemented with 5 ul of 10XPCR buffer, 1 ul of each dNTP (10 mM), 1 ul each of 40 µM primer solutions, 1.25 units of Taq polymerase, and water, to a total volume of 50 ul. Each mixture was heated for five minutes at 94° C. Amplification was then carried out for 30 cycles (MAGE-1: 1 minute at 94° C., 3 minutes at 72° C.; MAGE-2: 1 minute at 94° C., 2 minutes at 67° C.; MAGE-3: 1 minute at 94° C., 4 minutes at 72° C.). Cycling was concluded, in each case, with a final extension at 72° C. for 15 minutes. A 10 ul sample of each reaction was run on a 1% agarose gel, and visualized by ethidium bromide fluorescence. To ensure that RNA was not degraded, a PCR assay with primers specific for β-actin was carried out, following the listed protocols, except that only 20 cycles were carried out with the annealing step at 65° C. Date are summarized in the Table which follows:

TABLE 1

Expression of gene MAGE-1, 2 and 3 in lung tumors

| | Proportion of positive samples | | |
|---|---|---|---|
| | MAGE-1 | MAGE-2 | MAGE-3 |
| Non-small cell lung cancer | 16/46 | 16/46 | 14/46 |
| squamous cell carcinoma | 8/26 | 6/26 | 7/26 |
| adenocarcinoma | 8/18 | 9/18 | 7/18 |
| large cell carcinoma | 0/2 | 1/2 | 0/2 |
| Small cell cancer | 1/3 | 2/3 | 2/3 |
| Normal lung samples | 0/8 | 0/8 | 0/8 |

EXAMPLE 2

The previous example showed how to identify expression of various MAGE genes. This example explains quantitation of the expression.

First, cDNA was synthesized in the same way described in example 1, except that the oligo dT consisted solely of dT15, and the reaction mixture was preincubated at room temperature for 10 minutes to optimize annealing. Also, following the incubation, the transcriptase activity was terminated by heating the mixture at 95° C. for 15 minutes. PCR amplification was carried out, by combining 5 ul of 10x PCR buffer, 0.5 ul of a 2.5 mM dNTP mix, 0.2 μCi of a $\alpha^{32}$P-dCTP, 0.5 ul of each primer (40 μM solution), 1.25 units of Taq polymerase, and water, to a total of 50 ul. The mixtures were chilled on ice, and then 5 ul of chilled cDNA solution (100 ng total RNA) were added thereto. The mixture was heated to 94° C. for five minutes, and 24 cycles of amplification were carried out (one minute at 94° C., three minutes at 72° C. per cycle). Cycling concluded with a final extension at 72° C., for 15 minutes. A 15 ul sample of PCR product was run on an agarose gel which was then fixed in 10% trichloroacetic acid for 30 minutes, dried, and then exposed to a phospho-screen for 90 minutes before scanning by Phosphor-Imager to measure incorporated $^{32}$P. This was compared to the incorporations from various dilutions of RNA of reference melanoma cell line MZ2-MEL-3.0.

Quantitative measurements of β-actin messenger and "GAPDH" (i.e., glyceraldehyde 3-phosphate dehydrogenase) was carried out on each cDNA sample, under similar conditions. The one difference was that only 18 amplification cycles were carried out. A separate PCR reaction was set up with primers for β-actin and GAPDH, with only β-actin used for normalization. Results were expressed via formula:

$$100 \times \frac{\left[\frac{\text{MAGE-1-S}}{\text{Actin-S}}\right]}{\left[\frac{\text{MAGE-1-MEL}}{\text{Actin-MEL}}\right]}$$

where:
S=product from tumor sample
MEL=product from MZ2-MEL 3.0

Figure 2:
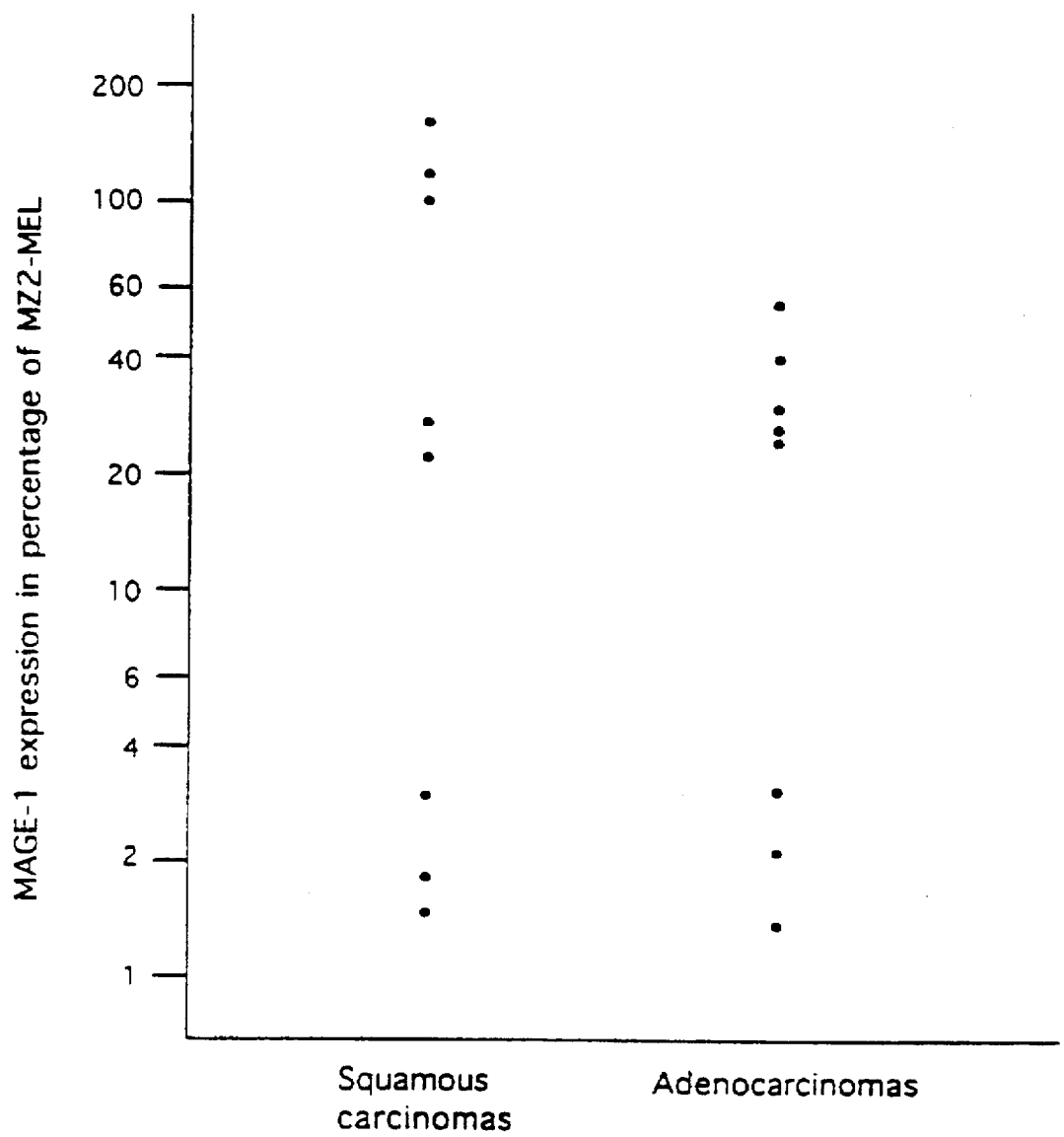
FIG. 2 presents data pertaining to quantitative measurement of MAGE-1 expression.

The results obtained were comparable to those obtained previously with melanoma tumors. Level of expression varied, from 1 to 160% of the amount expressed by the reference cell line. FIG. 2 presents some of these results (i.e., normalized results, relative to levels of β-actin expression). Values are percent of the level of MAGE-1 expression measured with RNA of the reference line MZ2-MEL-3.0. Values are for MAGE-1 positive tumors of Table 2). Table 2, which follows, summarizes patterns of expression for various tumors.

TABLE 2

Pattern of expression of genes MAGE-1,2 and 3 by MAGE-positive lung tumor samples

| | MAGE-1° | MAGE-2 | MAGE-3 |
|---|---|---|---|
| Squamous cell carcinoma | | | |
| LB 175 | ++ | ++ | |
| LB 195 | + | ++ | +++ |
| LB 178 | ++ | − | − |
| LB 182 (A1)* | + | − | |
| LB 206 | +++ | + | ++ |
| LB 321 | + | − | − |
| LB 323 | +++ | + | |
| LB 424 | + | − | + |
| LB 425 | − | + | |
| LB 498 (A1) | +++ | − | − |
| LB 557 | − | − | +++ |
| Adenocarcinoma | | | |
| LB 117 (A1) | + | ++ | ++ |
| LB 212 | ++ | + | − |
| LB 264 (A1) | +++ | ++ | |
| LB 292 | − | ++ | +++ |
| LB 306 | ++ | + | ++ |
| LB 322 | − | + | + |
| LB 474 (A1) | + | ++ | − |
| LB 497 | ++ | +++ | |
| LB 510 | +++ | − | − |
| LB 558 (A1) | + | + | + |
| Large cell carcinoma | | | |
| LB 259 | − | + | − |
| Small cell lung cancer | | | |
| LB 444 | − | ++ | +++ |
| LB 648 (A1) | + | ++ | +++ |

The foregoing examples show that expression of at least one of MAGE-1, 2 and 3 is correlated to lung adenocarcinomas, e.g.. One aspect of the invention, then, is a method for determining these lung adenocarcinomas by assaying a sample for expression of at least one of MAGE-1, 2 and 3. As MAGE genes are nearly without exception expressed only by tumor cells, there can be no question but that expression of a MAGE gene or genes is indicative of cancer. The fact that the cancer is the lung adenocarcinoma is easily ascertainable, as adenocarcinoma cells have distinct morphologies which are identifiable by the skilled artisan. Similarly, the fact that the tumor of interest is a lung adenocarcinoma as compared to a tumor from a different body part is self evident; one does not find lung adenocarcinoma in, e.g., large intestine tissue.

The assay for the MAGE gene can take many forms. Most preferably, the assay is done via determining gene expression, such as by determining mRNA transcription products. For example, amplification protocols, including but not being limited to polymerase chain reaction (PCR), and ligase chain reaction (LCR), are preferred. The assay can also be carried out using nucleic acid molecule probes, which are labelled or unlabelled, and which specifically hybridize to sequences characteristic of the MAGE gene of interest. Labelling nucleotide probes is well known to the art, labels including radioactive, fluorescent, chromophoric, magnetic, and other identifiable materials. Antibodies, haptens such as biotin, (strept)avidin, digoxin, digoxigenin, and so forth, can all be used. Non-labelled probes can also be used. In such a case, the probes will form a double stranded molecule with their target. Any remaining single stranded material can be enzymatically digested, and when something remains, it is a sign of MAGE expression. For the case of polymerase chain reaction or other methodologies where a primer or primers are required, the molecules represented by SEQ ID NO: 1 and SEQ ID NO: 2 are especially preferred for MAGE-1, SEQ ID NO: 3 and 4 for MAGE-2 and SEQ ID NOS: 5 and 6 for MAGE-3. Similarly, these molecules are preferred as probes.

Quantitation of MAGE expression is shown herein as well. This is an important feature of the invention because in a given tumor sample (as compared to tumor cell lines) there will always be an undetermined proportion of normal cells.

One may also assay for the expression product of the MAGE gene, e.g., the tumor rejection antigen precursor protein, via assays such as immunoassays. See, e.g., U.S. patent application Ser. No. 08/190,411 filed Feb. 1, 1994, and Chen, et al., Proc. Natl. Acad. Sci. USA 91(3): 1004-1008 (1994), both of which are incorporated by reference, teaching MAGE-1 specific mAbs.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

---

We claim:

1. Method for screening a sample of lung tissue for possible presence of adenocarcinoma, comprising assaying said sample and determining expression of a gene which codes for a tumor rejection antigen precursor selected from the group consisting of MAGE-1, MAGE-2 and MAGE-3, wherein expression of said gene is an indication of possible presence of adenocarcinoma in said sample.

2. The method of claim 1, comprising determining expression of said tumor rejection antigen precursor via nucleic acid molecule amplification.

3. The method of claim 1, comprising determining expression of said tumor rejection antigen precursor via polymerase chain reaction.

4. The method of claim 1, comprising determining expression of said tumor rejection antigen precursor via a labelled nucleotide probe which specifically hybridizes to a sequence coding for said tumor rejection antigen precursor.

5. The method of claim 3, wherein said polymerase chain reaction is carried out with at least one nucleotide primer selected from the group consisting of SEQ ID NO: 1 and SEQ ID NO: 2.

6. The method of claim 3, wherein said polymerase chain reaction is carried out with at least one nucleotide primer selected from the group consisting of SEQ ID NO: 3 and SEQ ID NO: 4.

7. The method of claim 3, wherein said polymerase chain reaction is carried out with at least one nucleotide primer selected from the group consisting of SEQ ID NO: 5 and SEQ ID NO: 6.

8. The method of claim 4, wherein said labelled nucleotide probe consists of labelled SEQ ID NO: 1 or labelled SEQ ID NO: 2.

9. The method of claim 4, wherein said radiolabelled nucleotide probe consists of SEQ ID NO: 3 or SEQ ID NO: 4.

10. The method of claim 4, wherein said labelled nucleotide probe consists of labelled SEQ ID NO: 5 or labelled SEQ ID NO: 6.

11. Method for determining presence or amount of expression of a tumor rejection antigen precursor selected from the group consisting of MAGE-1, MAGE-2 and MAGE-3 in a lung adenocarcinoma, comprising contacting said sample with an agent which reacts with a nucleic acid molecule coding for said tumor rejection antigen precursor or an expression product of said gene, and determining reaction of said agent as a determination of presence or amount of said tumor rejection antigen precursor.

* * * * *